US011813618B2

(12) United States Patent
Jackson et al.

(10) Patent No.: US 11,813,618 B2
(45) Date of Patent: Nov. 14, 2023

(54) MONOLITHIC INTEGRATED MESH DEVICE FOR FLUID DISPENSERS AND METHOD OF MAKING SAME (71) Applicant: University College Cork—National University of Ireland, Cork, Cork (IE)

(72) Inventors: Nathan Jackson, Cork (IE); Alan Mathewson, Cork (IE); Zbigniew Olszewski, Cork (IE)

(73) Assignee: University College Cork—National University of Ireland, Cork (IE)

( * ) Notice: Subject to any disclaimer, the term of this patent is extended or adjusted under 35 U.S.C. 154(b) by 105 days.

(21) Appl. No.: 16/082,027

(22) PCT Filed: Mar. 6, 2017

(86) PCT No.: PCT/EP2017/055222
§ 371 (c)(1),
(2) Date: Sep. 4, 2018

(87) PCT Pub. No.: WO2017/149165
PCT Pub. Date: Sep. 8, 2017

(65) Prior Publication Data
US 2020/0290077 A1  Sep. 17, 2020

(30) Foreign Application Priority Data
Mar. 4, 2016  (GB) ...................... 1603823

(51) Int. Cl.
*B05B 17/06* (2006.01)
*B05B 17/00* (2006.01)
(52) U.S. Cl.
CPC ...... *B05B 17/0653* (2013.01); *B05B 17/0646* (2013.01); *B06B 2201/77* (2013.01)

(58) Field of Classification Search
CPC ............ B05B 17/0661; B05B 17/0646; B05B 17/0653; B06B 2201/77
See application file for complete search history.

(56) References Cited

U.S. PATENT DOCUMENTS 5,828,394 A * 10/1998 Khuri-Yakub ......... B41J 2/1634
347/72
6,546,927 B2   4/2003 Litherland et al.
(Continued)

FOREIGN PATENT DOCUMENTS

WO   WO2011/156556 A2   12/2011

OTHER PUBLICATIONS

International Search Report and Written Opinion, International Application No. PCT/EP2017/055222, dated Jun. 9, 2017 (15 pages).

(Continued)

*Primary Examiner* — Tuongminh N Pham
(74) *Attorney, Agent, or Firm* — Occhiuti & Rohlicek LLP

(57) ABSTRACT

The invention provides a monolithic integrated mesh device for atomization or pumping of a fluid or liquid comprising a plurality of apertures and a piezoelectric material. The piezoelectric material is bonded to the mesh device at an atomic scale. In one embodiment the monolithic microfabricated device of the invention includes piezoelectric material that eliminates the need for expensive assembly process and improves reliability. This also has advantage of requiring lower operating voltage and less complicated circuitry.

13 Claims, 10 Drawing Sheets

Micro-fabricated mesh

Micro-fabricated mesh monolithically integrated with piezo-actuator (a)

(b)

(56) References Cited

U.S. PATENT DOCUMENTS

| | | | |
|---|---|---|---|
| 2007/0080245 A1* | 4/2007 | Lin | B41J 2/14201 |
| | | | 239/533.1 |
| 2007/0158477 A1 | 7/2007 | Wu et al. | |
| 2008/0239025 A1 | 10/2008 | Wang | |
| 2009/0272818 A1 | 11/2009 | Valpey, III et al. | |
| 2010/0331769 A1* | 12/2010 | Nisato | A61M 5/30 |
| | | | 604/39 |
| 2011/0037813 A1 | 2/2011 | Nakatani | |
| 2013/0214879 A1* | 8/2013 | Gorisse | H03H 9/56 |
| | | | 333/191 |
| 2014/0063095 A1 | 3/2014 | Yokoyama et al. | |

OTHER PUBLICATIONS

Joseph C. Doll et al., "Aluminum nitride on titanium for CMOS compatible piezoelectric transducers," J Micromech Microeng. 20(2):25008, 20 pages (2010).

* cited by examiner

Prior Art

Figure 1a

Prior Art

Micro-fabricated mesh (a)

Micro-fabricated mesh monolithically integrated with piezo-actuator (b)

Figure 5

Schematic of micro-fabricated mesh

Figure 6

Schematic of micro-fabricated mesh monolithically integrated with piezo-actuator

Figure 7

Silicon Mesh with plurality of holes
and bulk-ring around bulk-ring around (mesh support)

Monolithic integrated mesh with piezoelectric material, plurality of holes and bulk-ring around

Step 3: Deposition and etching of second metal layer

Figure 13

Step 4: Etching of apertures (i.e. holes) in silicon down to oxide layer

MONOLITHIC INTEGRATED MESH DEVICE FOR FLUID DISPENSERS AND METHOD OF MAKING SAME

CROSS REFERENCE TO RELATED APPLICATION

This application is the national phase under 35 USC 371 of international application No. PCT/EP2017/055222, filed Mar. 6, 2017, which claims the benefit of the priority date of British application No. 1603823.4, filed Mar. 4, 2016. The contents of the aforementioned applications are incorporated herein in their entirety.

FIELD

The disclosure relates to a mesh device. In particular the disclosure relates to a micro-fabricated mesh device for atomization or pumping of a fluid or liquid.

BACKGROUND

Atomization creates an aerosol from liquid, and is used in numerous applications. During the atomization process the liquid is in contact with mesh which may be excited into mechanical vibration by the actuator (actively vibrating). During this mechanical vibration the liquid is pumped or extruded through a plurality of holes or apertures in the mesh and is output on the other side of the mesh as an aerosol, as the fluid ligaments recoil into spheres of droplets. Alternatively atomisation can be achieved with the mesh facilitating extrusion of liquid provided momentum by a sonotrode or vibrating horn (passive vibrating/static mesh). One application is as a nebulizer (or drug delivery) device. A vibrating mesh device is one of a number of devices currently used in nebulizer technology. Others include ultrasonic and jet nebulizers.

Current vibrating mesh devices are fabricated using laser drilling or electroforming. Such devices use bulk commercial piezoelectric actuators to vibrate the mesh in a specific mode which atomizes the liquid. The current devices are expensive to manufacture, poor repeatability and they do not have the capability of integrating piezoelectric actuator, advanced circuitry or sensors. Advanced circuitry is desired to control the oscillations of the plurality of apertures making up the mesh which is complex and difficult to implement.

Examples of atomization device assemblies are disclosed in EP2886185; EP0546964; U.S. Pat. No. 4,850,534; JP2004190537; WO0176762; U.S. Pat. Nos. 5,152,456; 6,235,177; WO2008/029216; JP2002318193; EP1022063; JPH0780369; WO2016/150715 A1; WO2011/154394; EP 1 813 428B1; US 2003/0112300 A1; U.S. Pat. No. 7,226,151 B2 and US2013/0120505.

Figure 1A:
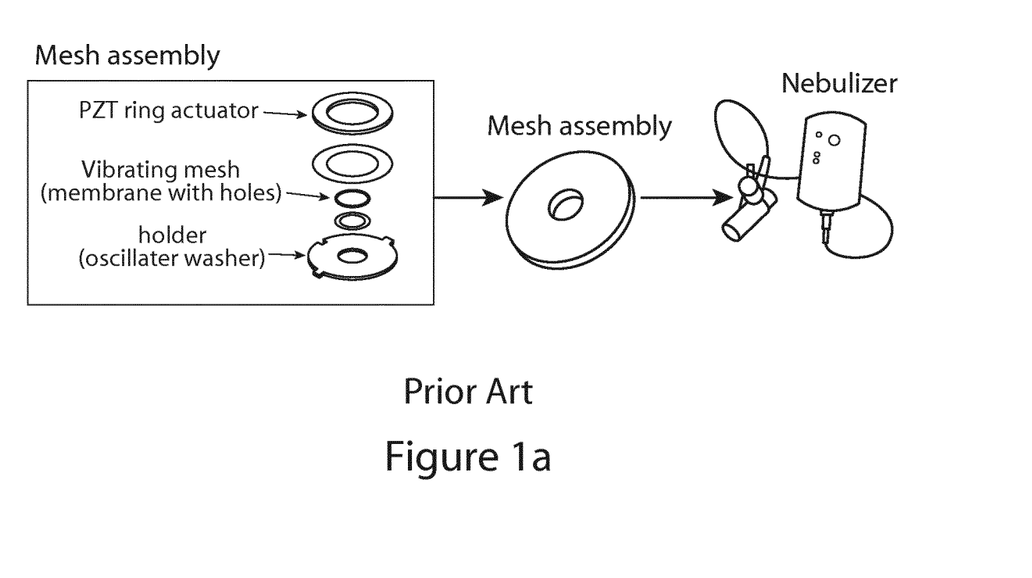
Figure 1B:
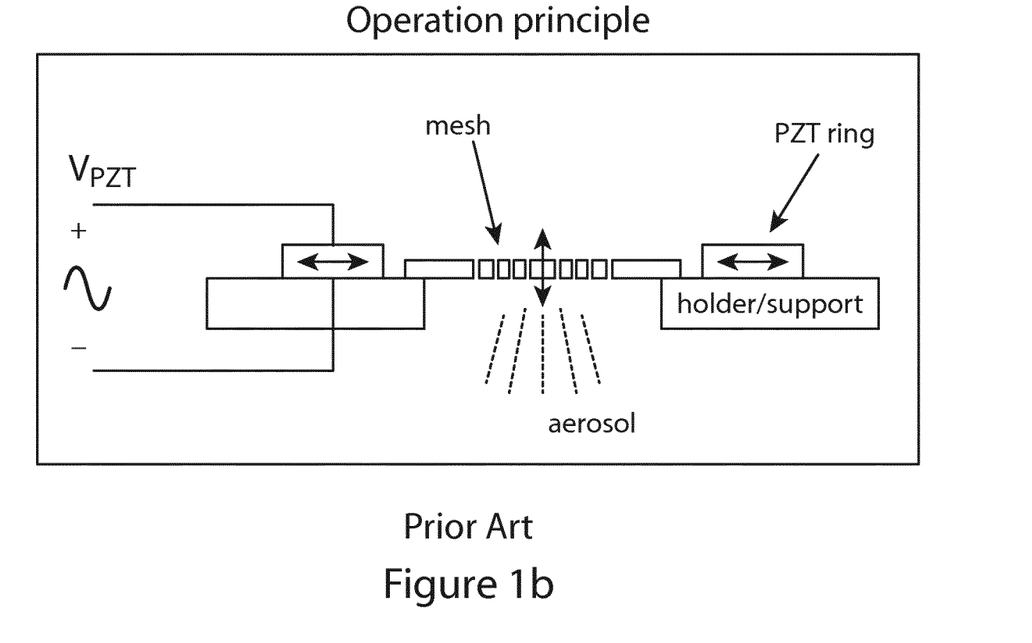

In a typical prior-art implementation of a vibrating mesh, as shown in FIGS. 1a and 1b, an assembly process is used to create a head of an aerosol generator. In the assembly process the mesh, usually metal, is attached to a metallic holder (also called a washer) by gluing, brazing, or welding, etc. Also a piezoelectric ring actuator is glued to the metallic holder. In practice, an additional two rings within the assembly are required to attach the PZT ring actuator to the holder. It must be conductive material so the bottom side of the PZT can be electrically biased through applying the voltage to the holder that is made of metal, the second ring is just a regular adhesive to attach the mesh to the holder. As shown in FIG. 1b when an AC voltage is applied to the piezoelectric actuator it starts to vibrate laterally and the acoustic energy is transferred through the holder to the mesh that is excited to mechanical vibration causing an aerosol generation. The assembly process requires different components and adhesives to be fabricated by different manufacturers and delivered to the assembly line. This significantly adds to the cost and reliability of the assembly. A number of problems exist with the assembled components, namely reliability issues during operation of the aerosol head because components can dis-assemble or the intermediate layer such as adhesives can change properties during operation and cause device not to perform properly i.e. if the glue changes the properties than the effective device stiffness and its frequency and displacement also change. This directly affects the generated aerosol in operation.

It is therefore an object to provide an improved mesh device and method of making same.

SUMMARY

According to the invention there is provided, as set out in the appended claims, a monolithic integrated mesh device for atomization of a fluid or liquid comprising a plurality of apertures and a piezoelectric material.

The invention provides a mesh device which monolithically combines thin film deposited piezoelectric material that can be deposited directly on the mesh and near at least one aperture. Advantageously the integrated mesh device comprises a thin-film piezoelectric actuator integrated directly with the mesh in single micro-fabrication process. Thus monolithic integration between piezo-actuator and mesh is achieved, where monolithic integration is bonding at the atomic level.

The invention provides a monolithic integrated mesh as a single-chip device comprising a structural material, such as silicon, electrode materials, e.g. titanium, aluminium, etc., and a piezoelectric material e.g. aluminium nitride, zinc oxide, etc., and is made in a single fabrication process on a base substrate such as standard Silicon or Silicon On Insulator (SOI) substrate. Fabrication comprises a number of photolithography steps for materials, deposition and etching that are used in semiconductor industry. There is no assembly process required, such as using a glue or bonding, as disclosed in the aforementioned prior art technology and overcoming the problems associated with mesh assemblies.

The microfabrication technique reduces costs and increase repeatability and reliability. In one embodiment a (Complementary Metal Oxide Semiconductor) CMOS compatible device allows a complete and integrated system can easily incorporate at least one sensor and advanced circuitry. The mesh device can be used for controlling the size and volume of particles.

The mesh device, and method of making the device, according to the invention provides a number of advantages; namely reduces the number of steps arising from the assembly process/interconnect of different system components in the prior art.

Moreover, a holder is not required and the mechanical energy from the piezo-actuator is directly transferred to the mesh in use. The piezo-actuator does not touch other system components other than the mesh, therefore the overall energy losses in the system is limited to absolute minimum, which is not the case in multi-component assembled devices. This allows for most efficient transfer of electrical energy from a provided bias into mechanical energy acting on the liquid during atomization process. The integrated mesh device can be built on different substrates suitable for thin film piezoelectric materials deposition. One such substrate can be silicon, thus the entire device can be fabricated using standard high volume production methods used in MEMS and CMOS technologies. It will be appreciated that other semiconductor materials, and also metals or polymers can be used if are suitable as a substrate layer for piezoelectric material to be deposited.

In one embodiment the mesh device comprises silicon.

In one embodiment the piezoelectric material comprises a thin film piezoelectric material deposited on the mesh device.

In one embodiment the size of the apertures are selected to control the droplet size of the atomized fluid or liquid.

In one embodiment at least one aperture surface is treated to increase the hydrophobic properties of the at least one aperture.

In one embodiment the piezoelectric material covers at least a part of the, or a whole, mesh.

In one embodiment the piezoelectric material is selected to control a plurality of different resonant modes of the device.

In one embodiment application of a voltage to the piezoelectric material induces displacement of the mesh device to control the vibration frequency and/or displacement.

In one embodiment the piezoelectric material comprises CMOS compatible piezoelectric material.

In one embodiment the mesh comprises an integrated sensor.

In one embodiment the piezoelectric material is adapted to be uniquely patterned on the mesh device to control the mode of operation of the mesh device.

In one embodiment the mesh device is made using a microfabrication technique.

In one embodiment the mesh device comprises at least one of: glass, metal, ceramic or a polymer.

In a further embodiment there is provided an integrated vibrating mesh device for atomization of a liquid comprising a plurality of apertures made using a microfabrication process and wherein the mesh device comprises at least one of: silicon, glass, metal, ceramic or a polymer.

It will be appreciated that the invention provides a silicon based vibrating mesh device. The silicon mesh offers less expensive devices, increases yield, increases reliability of aperture or hole dimensions, options to optimize aperture or hole size and shape, and increase aperture/hole density for higher flow rate.

The micro-fabricated device of the invention can include deposited piezoelectric materials, which will eliminate the need for expensive assembly process. This also has advantage of requiring lower voltage (less complicated circuitry). By depositing the piezoelectric material optimized patterning of the material can be developed. Previously nebulizer industry just use commercial piezoelectric rings not integrated with mesh.

In a further embodiment there is provided a method of making a monolithic integrated mesh device comprising the steps of:

providing a substrate layer;

depositing a piezoelectric material layer on said substrate; and etching said substrate layer and piezoelectric layer to fabricate a plurality of apertures and form said monolithic integrated mesh device.

In another embodiment there is provided a method of making a monolithic integrated mesh device comprising the steps of:

providing a substrate layer;

depositing at least two layers to form a piezoelectric stack comprising at least one metal layer and at least one piezoelectric layer on said substrate layer; and patterning of the piezoelectric stack layer and substrate layer to form a piezoelectric actuator and a plurality of apertures to form said monolithic integrated mesh device.

By using CMOS compatible piezoelectric materials and silicon-based process one can fabricate the circuitry on the same die as the vibrating mesh, which will cut the cost to make nebulizers significantly by having all the components on one die. The device of the invention can include integrated smart sensors.

In one embodiment the invention integrates a thin-film piezoelectric material onto a mesh, and using CMOS compatible materials add functionality such as control circuitry and sensors to the mesh device.

The micro-fabrication technique of the invention can be used to manufacture mesh devices from various substrates such as silicon that can directly replace current mesh devices. Alternatively, a monolithic integrated mesh device that will not require the assembly process and have better performance can be used. Using micro-fabrication techniques to create the aperture/holes will reduce pitch size and hole dimensions which may facilitate a higher flow rate and smaller droplets. In nebulizers, this can allow drugs that exhibit unfavourable physicochemical (surface tension and viscosity) properties to be more easily atomized.

BRIEF DESCRIPTION OF THE DRAWINGS

The invention will be more clearly understood from the following description of an embodiment thereof, given by way of example only, with reference to the accompanying drawings, in which:—

FIGS. 1*a* and 1*b* illustrates a prior art vibrating mesh assembly;

FIG. 2*a* illustrates 3D FEM model of an integrated mesh device for atomization of a fluid or liquid, comprising of a silicon membrane with a thin film of piezoelectric material deposited on top; FIG. 2*b* also illustrates the FEM results showing the device operating in 02 resonance mode;

FIG. 3 illustrates results from the 3D model described in FIG. 2, and shows the central displacement around the 02 resonance mode for three different diameters of an actuator;

FIG. 4 illustrates results from the 3D model; and shows the central displacement around the 02 resonance mode for one diameter of a piezoelectric actuator and for five different amplitudes of driving voltages;

FIG. 5*a* illustrates a SEM image of a micro-fabricated mesh device according to one embodiment of the invention.

FIG. 5*b* illustrates an image of micro-fabricated integrated mesh device according to other embodiment of the invention;

FIG. 6 illustrates a cross sectional view of micro-fabricated mesh device according to one embodiment of the invention;

FIG. 7 illustrates a cross sectional view of micro-fabricated mesh device incorporating piezoelectric material, according to one embodiment of the invention FIGS. 8*a*, 8*b* and 8*c* illustrates a schematic top-view and cross-sectional view of a device utilizing the mesh in this invention;

FIGS. 9*a* and 9*b* illustrates a schematic top-view and cross-sectional view of a device utilizing the mesh in this invention;

DETAILED DESCRIPTION OF THE DRAWINGS

The invention provides a vibrating mesh aperture to atomize or pump a fluid or a liquid. The invention makes use of micro-fabrication techniques along with thin film piezoelectric materials to create a monolithic vibrating mesh aperture. Micro-fabrication techniques significantly reduce the cost of manufacturing the devices, the processes are highly repeatable and predictable, and CMOS compatible thin film piezoelectric material can be used to integrate it with at least on sensor. The devices can be made using standard CMOS and MEMS Silicon fabrication techniques, which includes optimization of aperture or hole dimensions and fabrication of the apertures or holes for the aperture device, as well as surface treatment of the aperture to alter the hydrophobicity of the aperture. The device of the invention can be embodied in a number of different ways:

Stand-Alone Mesh Aperture Embodiment

A vibrating mesh with a plurality of apertures can be micro-fabricated which can directly replace current mesh devices. The device does not include a thin film deposited piezoelectric material that forms the actuator, as reference below, but instead replaces current apertures and can be used with a bulk commercial piezoelectric actuator. The aperture can be fabricated out of various materials like silicon, glass, metals, ceramics, or polymers. An array of apertures/holes are then etched in the substrate with a specific aperture/hole shape and dimension to create micro-sized droplets during the atomization process.

The apertures or holes can be wet or dry etched or a combination of the two to control hole shape. For instance a KOH etch of a (100) Si substrate gives a precise etch at 54.7°, which is a repeatable process. Isotropic wet and dry etch techniques can also be used to create unique hole shapes. However, anisotropic dry etch of Si will have a near 80-90° profile. Hole or aperture shapes can be optimized by combining various wet and dry etch techniques. Thin film insulation material can also be included in the aperture as protection from contamination and can include surface treatment to prevent contamination or to control hydrophobicity.

The surfaces hydrophobicity of the mesh device can be altered by changing the surface energy through coatings of layers or various treatments. Coatings of hydrophobic or hydrophilic films can be deposited on the surface of the mesh membrane using various methods including chemical vapour deposition, Atomic layer deposition, dip coating, spin coating, aerosol spray, or physical vapour deposition. In addition surface treatments using different compositions of plasma gases and monomers can be used to alter the surface energy by changing surface topography and attachment of various functional groups at the atomic level.

Monolithic Vibrating Mesh Aperture Device with Integrated Piezoelectric Material A more advanced device integrates a standalone mesh aperture with a thin film piezoelectric material to create a monolithic vibrating mesh device. The thin film piezoelectric material can cover the entire device or have unique shapes to promote specific resonant modes.

An optimal pattern of piezoelectric material can be selected to enhance displacement of the membrane for specific resonant modes. The integration of the thin film piezoelectric material will give similar displacement as the stand alone aperture but with reduced voltage, which makes the circuitry to control the vibration simpler and uses less power. The thin film piezoelectric material can include PZT, PVDF, ZnO, AlN or any other piezo or ferroelectric materials. Aluminium Nitride however, is CMOS compatible so the entire fabrication can be performed in CMOS/MEMS fabrication facility allowing for integration of sensors or advanced circuitry.

Integration of Electronics or Sensors Embodiment

In an alternative embodiment the device can be combined with integrated electronics or sensors. By using a CMOS compatible piezoelectric material the entire system with built in control electronics and sensors can be developed. The integrated system can be batch fabricated from a single Silicon wafer, which significantly reduces the cost to manufacture the system. In addition sensors can be integrated to increase the functionality and performance of the nebulizer.

Example Nebulizer Embodiment

FIG. 1*a* a shows a typical nebulizer aperture which consists of a mesh that has specifically designed holes or apertures, it also consists holder and piezoelectric ring actuator. A bulk piezoelectric ring actuator and mesh are attached to the holder forming an aperture. An AC voltage applied to the piezoelectric ring causes the entire aperture to vibrate and this actuates the mesh, as illustrated in FIG. 1*b*. There are different resonance modes at which the mesh can operate, which is dependent on the frequency of the applied voltage. The resonant frequency of the mesh is dependent on the stiffness of the mesh.

Figure 5:
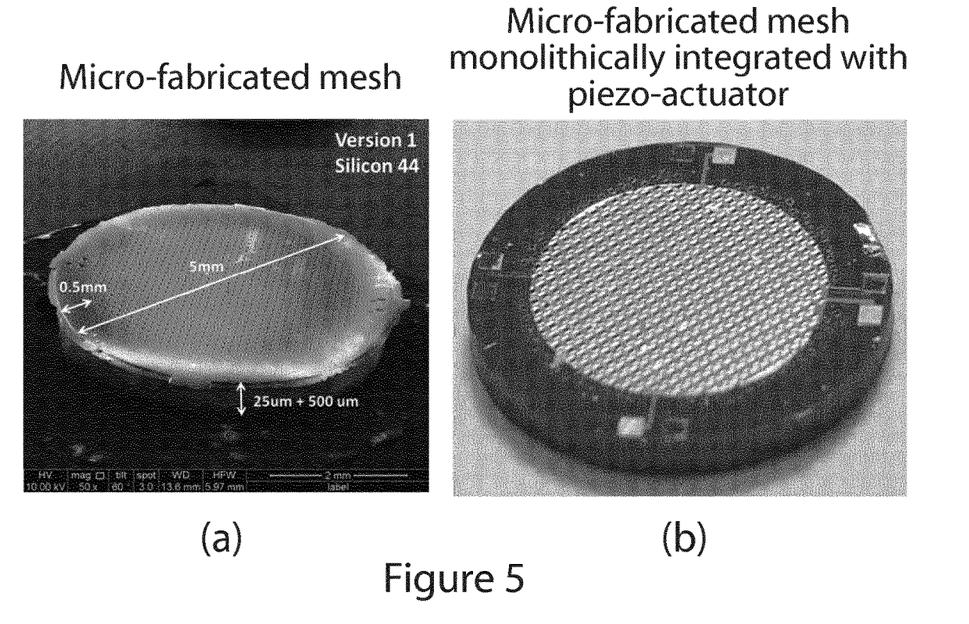

A first aspect of the invention, as described above, is to replace the current mesh with a micro-fabricated mesh. The mesh can be made from silicon, glass, polymers, ceramics, or metals. These devices can be used with existing assemblies using bulk piezoelectric ring actuator and holder. FIG. 5*a* shows a SEM image of the micro-fabricated mesh according to the invention using a silicon-on-insulator (SOI) wafer. The apertures/holes can be developed using either wet etch or dry etch techniques.

A second aspect of the invention is the integrated mesh device comprising a piezoelectric actuator formed as a single monolithic block. FIG. 5*b* shows an image of the micro-fabricated integrated mesh device.

The device operation was modelled using Finite Element Modelling (FEM) tool. Typically, for liquid nebulization the device operates optimally in the 02 resonance-mode (or near 02 resonance-mode).

Figure 2A:
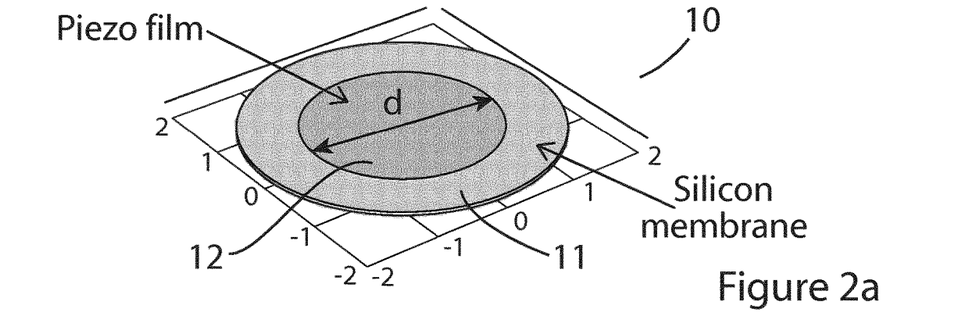
Figure 2B:
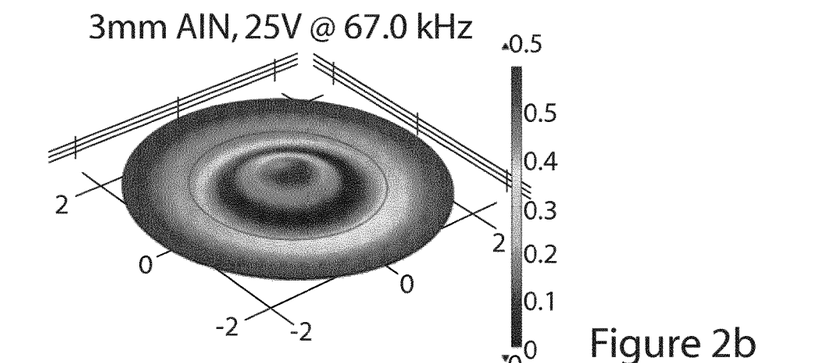

FIG. 2*a* illustrates a 3D FEM model of an integrated mesh device for atomization of a fluid or liquid indicated generally by the reference numeral 10. The mesh device 10 comprises of a silicon membrane 11 with a thin film of piezoelectric material 12 deposited thereon. FIG. 2*b* demonstrates the FEM model and simulated 02 resonance-mode of the integrated mesh for a 25 um thick silicon membrane of 5 mm diameter.

Figure 3:
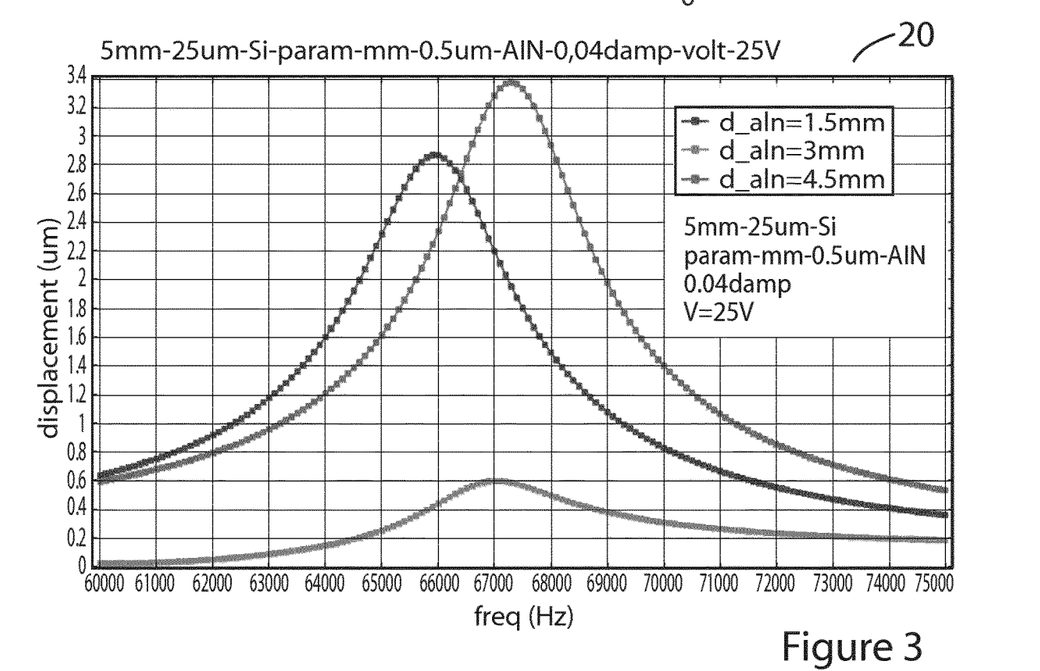

FIG. 3 shows results for three different patterns of the piezo-film actuator deposited on top of the membrane (i.e. the piezo-film patter has diameter of 4.5 mm, 3 mm, and 1.5 mm, as shown in FIG. 2*a*).

FIG. 3 shows the magnitude of the central deflection of the membrane for each pattern versus the signal frequency applied across the piezo-film indicated by the reference numeral 30. Note that the maximum deflection occurs at the resonance frequency that, as expected decreases with the piezo-film diameter due to lower effective stiffness of the device, i.e. 67.3 kHz, 67 kHz, and 65.9 kHz for 4.5 mm, 3 mm, and 1.5 mm piezo-film diameter, respectively. However, it was found that the magnitude of maximum displacement at resonance does not follows the same trend, i.e. the larges displacement is obtained for 4.5 mm pattern and the smallest displacement for the 3 mm pattern with the 1.5 mm pattern laying in between.

The results indicate that by optimizing the piezo-film pattern deposited on top of the membrane the displacement magnitude and/or the mode shape can be optimized. It is known that the displacement magnitude and mode shape of vibrating mesh devices can affect the flow rate of the device (i.e. liquid volume that is nebulized per unit of time) which is an important parameter from a medicinal efficacy point of view.

It is known that the displacement magnitude and mode shape of vibrating meshes can influence the integrity of the mesh and can lead to fractures propagating between apertures. Integration at the atomic level of silicon and piezoelectric material reduces the opportunity for fracture formation.

Figure 4:
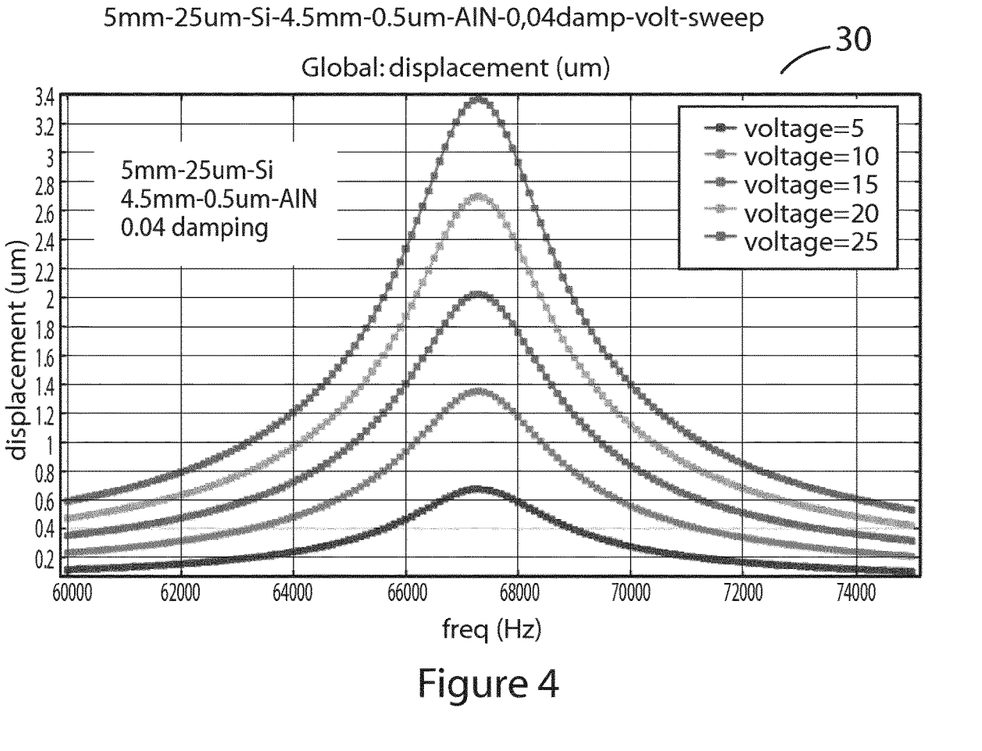

FIG. 4 shows the result for the device with 4.5 mm piezo-film pattern for different voltages indicated by the reference numeral 30. The results indicate that significant displacements can be achieved for relatively low voltages up to 25V. This low-voltage operation can be beneficial from the power consumption and driving circuit complexity point of view.

The ability to apply a variety of voltages and maintain displacement potential allows for the control of atomisation of liquids of varying physicochemical properties to produce a variety of droplet sizes and output rates.

FIG. 5a illustrates a SEM image of a micro-fabricated mesh device according to the stand-alone mesh aperture embodiment described above. FIG. 5b illustrates an image of micro-fabricated integrated mesh device to provide a monolithic vibrating mesh aperture device with integrated piezoelectric material.

Figure 6:
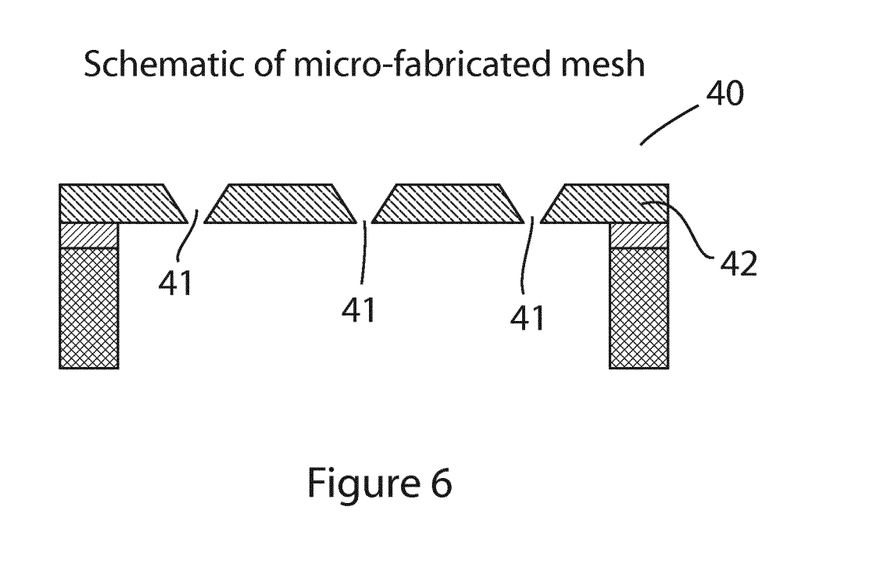
Figure 7:
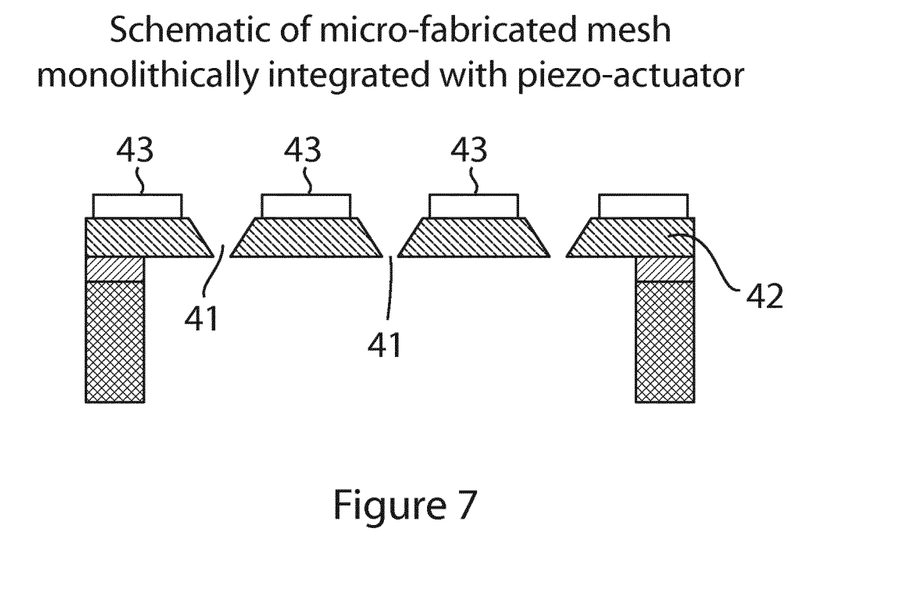

FIGS. 6 and 7 illustrates cross sectional views of a stand-alone mesh and integrated monolithic mesh device, according to embodiments of the invention.

The process for fabricating the device shown in FIG. 6 consists of starting with a silicon wafer 41 or silicon on insulator wafer, then patterning the mesh apertures/holes 42 using an etching technique and mask layer. After the apertures/holes are etched the backside silicon is removed and the device is released.

The process for fabricating the device shown in FIG. 7 consists of the same method shown in FIG. 6 with addition of a stack of metal layers 43 with a thin film piezoelectric material sandwiched in between them on top of the aperture plate.

The process has been optimised such that; a) there is maximal integration between layers, facilitating efficient and even energy transfer across the mesh and form an integrated monolithic device structure and b) the potential for liquid ingress between the layers is eliminated thereby mitigating the risk of delamination.

FIGS. 8a, 8b, 8c and 9a, 9b illustrate a number views of the mesh device for carrying out the present invention.

Figure 8A:
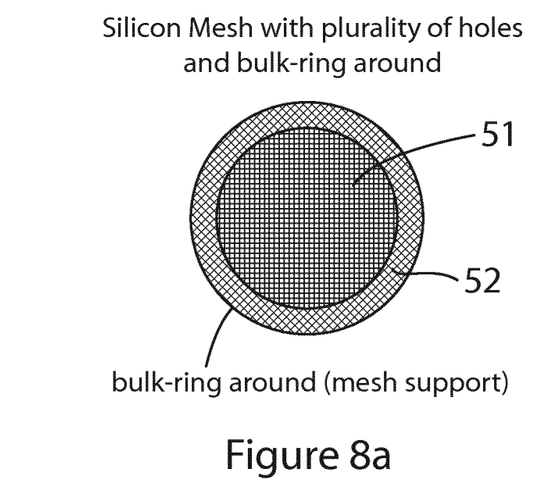
Figure 8B:
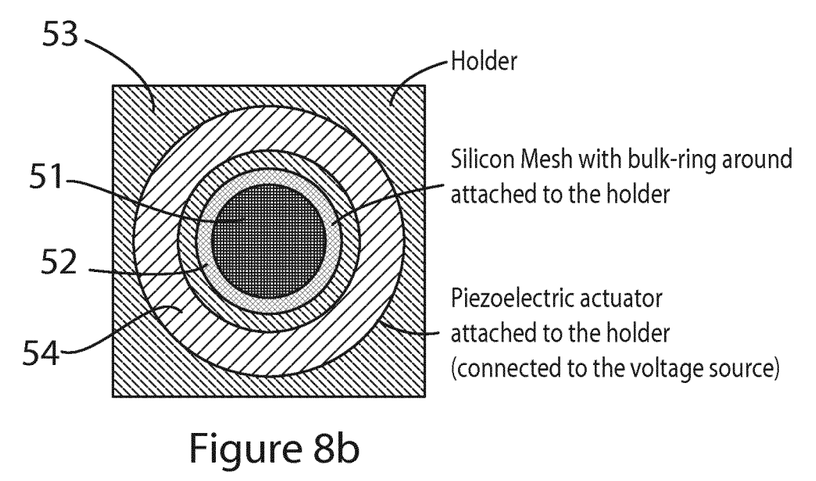
Figure 8C:
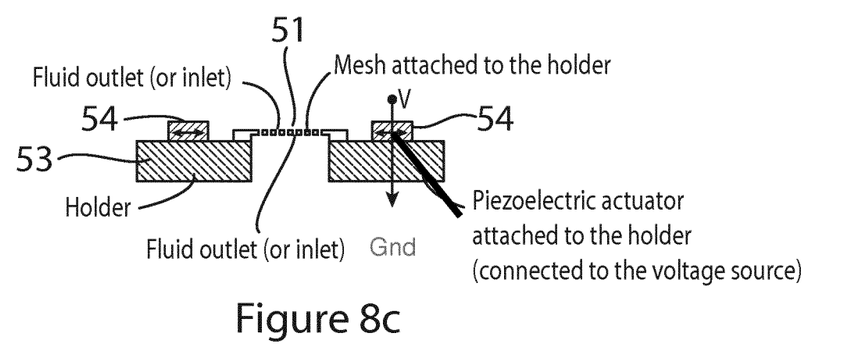

FIGS. 8a, 8b and 8c shows a schematic top-view and cross-sectional view illustrating a configuration in the case of utilizing a mesh without an integrated piezoelectric actuator but using an external piezoelectric actuator. The device is configured such that a mesh with a plurality of apertures/holes 51 and a bulk-ring 52 around (e.g. mesh support) is attached to a holder 53 and that the top surface of the holder 53 is present against the bottom surface of the mesh support and the bottom surface of an external piezoelectric actuator 54. The external piezoelectric actuator 54 can be connected to a driving voltage. In such a configuration, the mesh is contactable with fluid from the top or bottom and the fluid can be stored in a tank or container (not shown) also from either side of the device. When the piezoelectric actuator is caused to vibrate it also induces the vibration of mesh. When mesh vibrates the fluid from the tank passes through the plurality of holes in mesh.

Figure 9A:
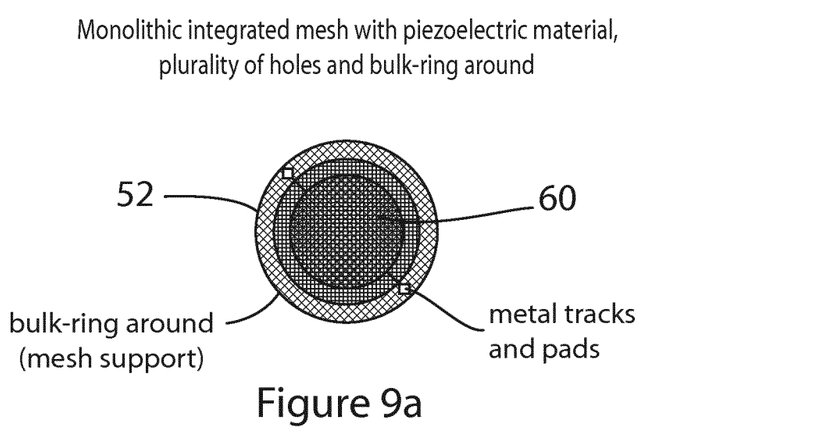
Figure 9B:
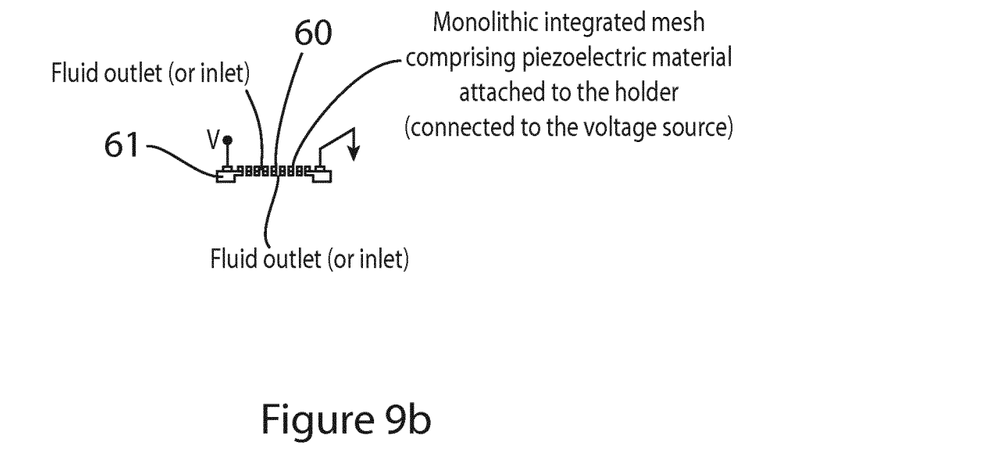

FIGS. 9a and 9b shows a schematic top-view and cross-sectional view illustrating a configuration in the case of utilizing a monolithic integrated mesh 60, incorporating an integrated piezoelectric actuator. The device configuration and operation is similar to that described in FIG. 8 but in this case the external piezoelectric actuator is not required and the integrated piezoelectric actuator can be connected to the driving voltage 61 to cause the vibration of mesh.

The present invention is not limited to the configurations shown in FIGS. 8 and 9 and the devices can be assembled in a different way for instance the holder can be attached from the other side of the mesh and also the holder could be integrated with the mesh in a single manufacturing process as well so no assembly step to assemble the mesh and holder is required. The mesh and holder form a single object. The driving voltage to the piezoelectric actuator can be delivered using different methods such as wire-bonding, pin-connectors, or can be directly delivered to the mesh through the tracks integrated on the holder.

Figure 10:
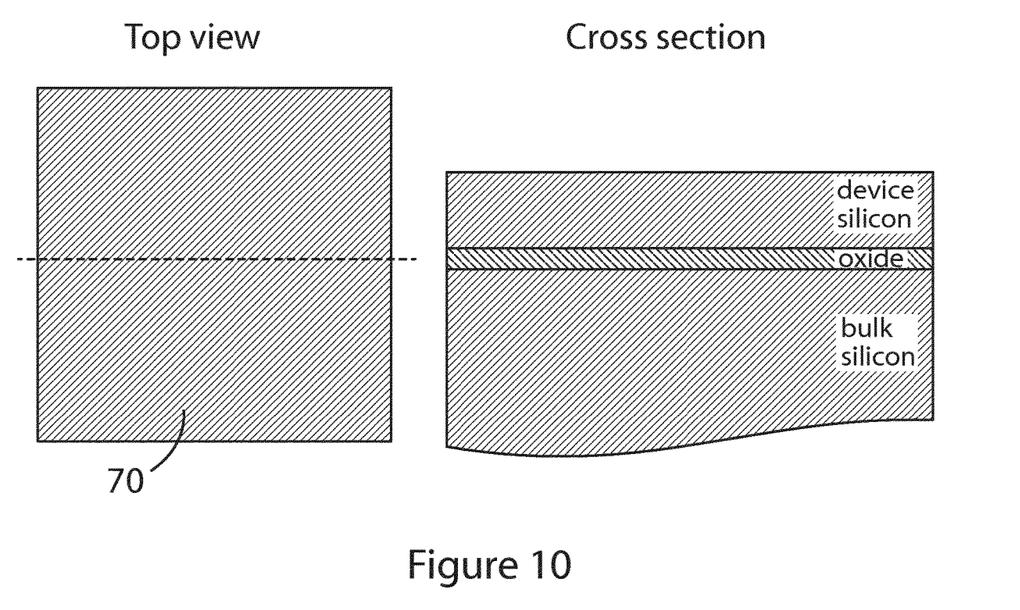
FIGS. 10 to 15 illustrates the fabrication process steps to make a monolithic integrated mesh device according to one embodiment of the invention.
Figure 11:
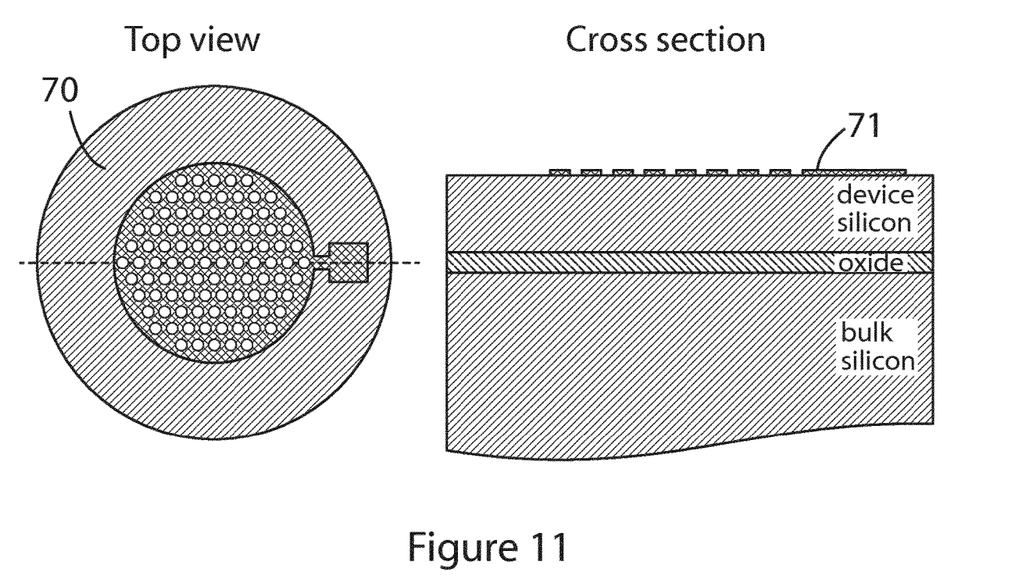
Figure 12:
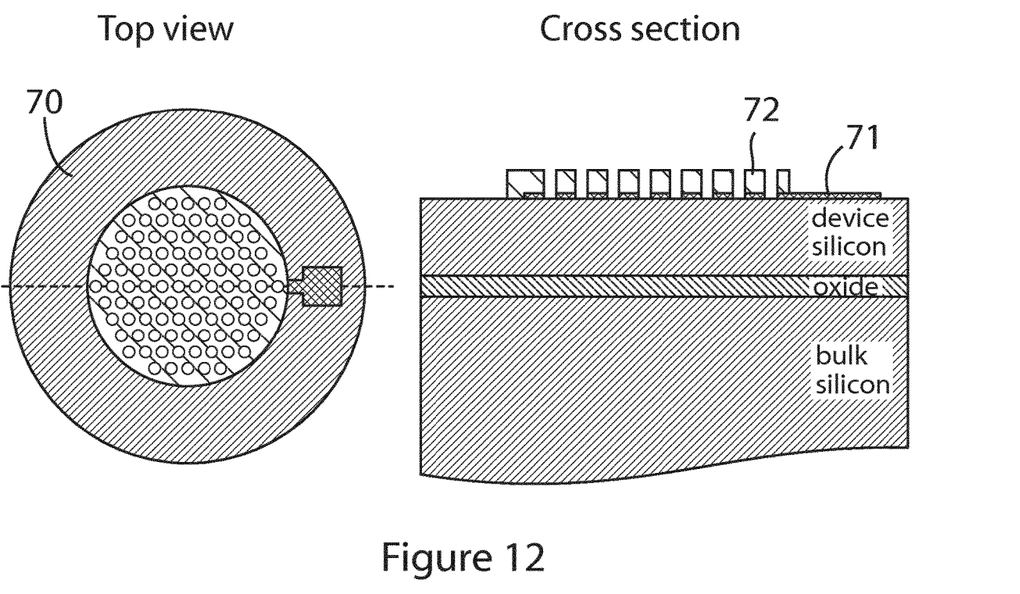
Figure 13:
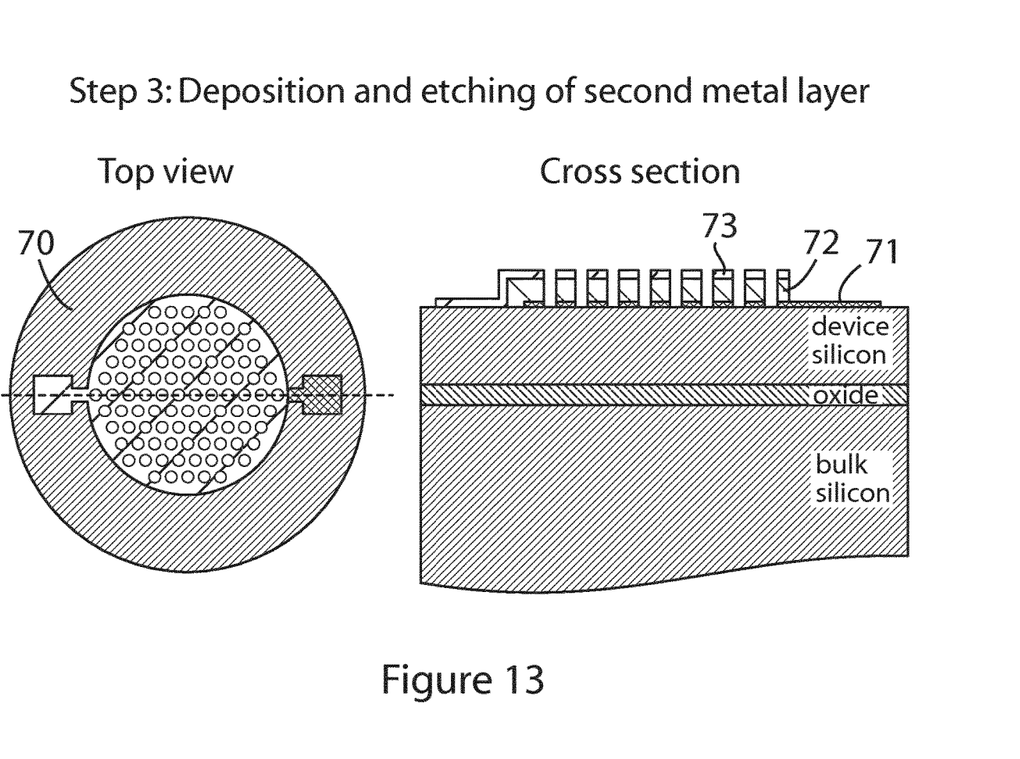
Figure 14:
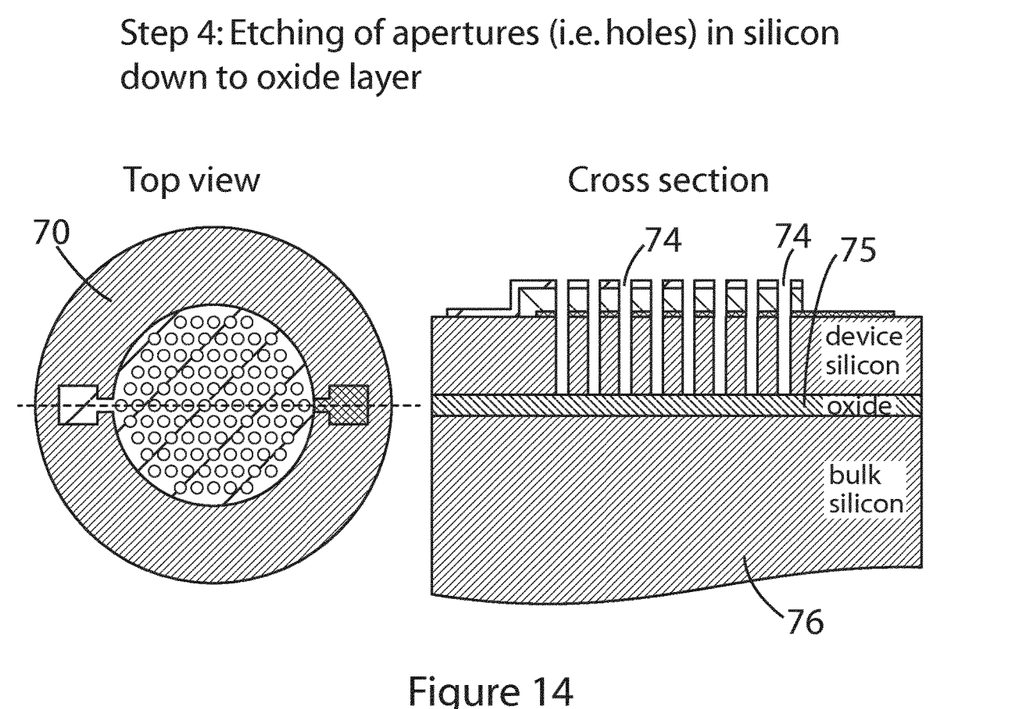
Figure 15:
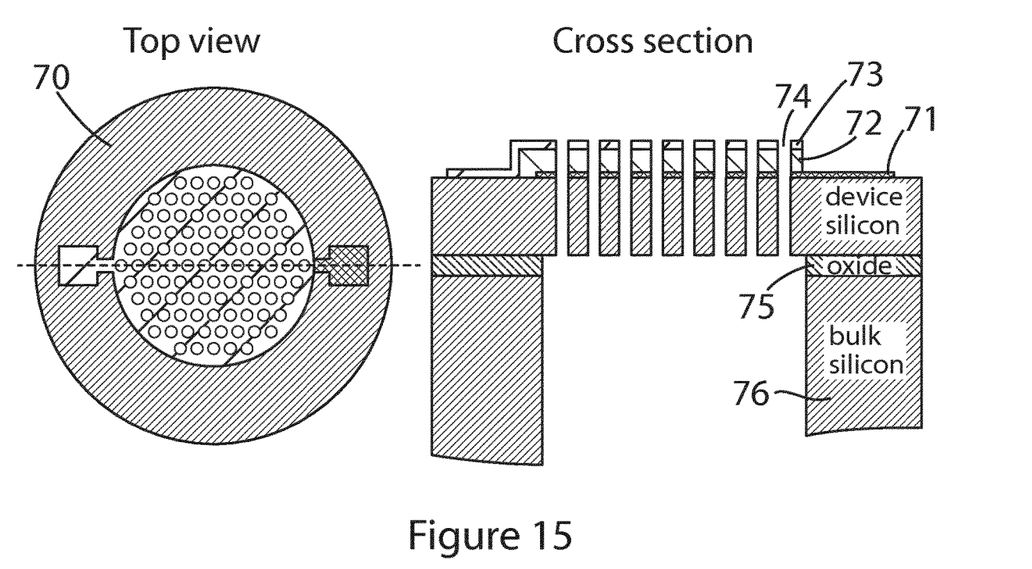
Figure 16:
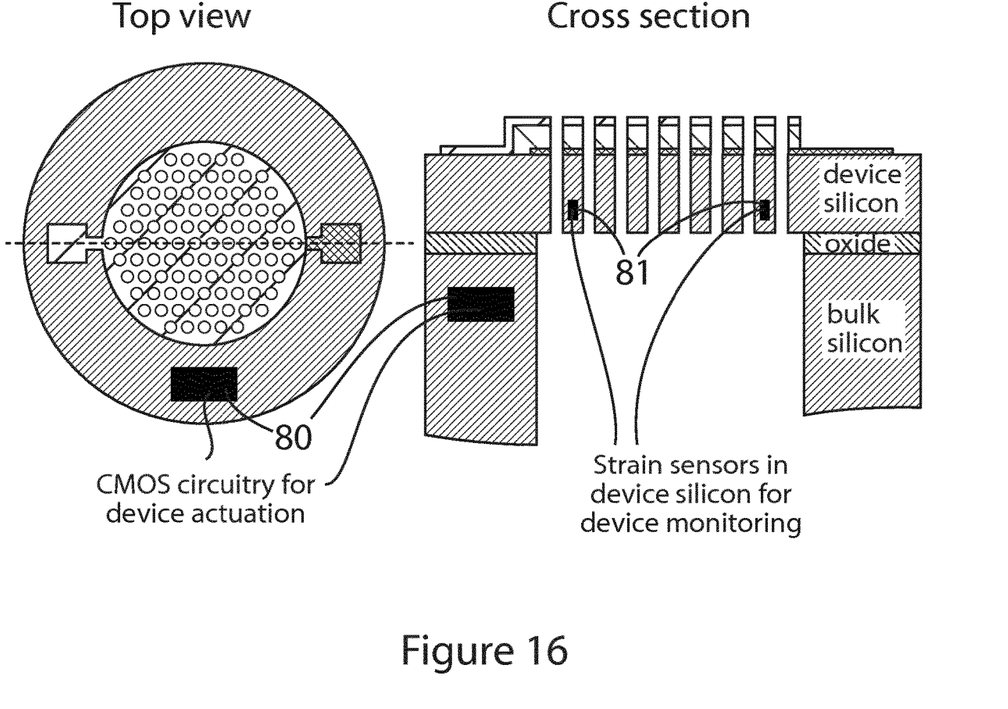
FIG. 16 illustrates at least one sensor/circuit configured to operate in conjunction with the monolithic integrated mesh device.

FIGS. 10 to 15 illustrate a fabrication process of a monolithic integrated mesh device on a substrate. FIG. 10 shows a top view and cross section view of the initial surface of the base substrate, for example a silicon or SOI wafer 70, which is prepared to deposit and etch a first metal layer. FIG. 11 shows a top view and cross section view for depositing and etching of a first metal layer 71. Metal can be deposited by a sputtering process that, on an atomic level, is the process whereby atoms are ejected from a metal target (material source that is to be deposited) and are deposited and bonded to the atoms on the surface of the substrate. FIG. 12 shows the piezoelectric material layer 71 and etching of the piezoelectric layer 72. FIG. 13 shows a second electrode material 73 layer that is deposited and patterned. In FIG. 14 the desired apertures are then etched in the device silicon and bulk silicon together down to oxide layer level 75. In FIG. 15 the oxide layer 75 and bulk silicon 76 is removed. The top and/or bottom electrodes can then be biased with an AC voltage which allows to excite the device into mechanical movement in a controlled manner.

In more detail, FIGS. 10 to 15 describes a typical sequence of processing steps to fabricate the device. In this non-limitative example, a Silicon on Insulator (SOI) substrate is used with a 25 µm thick device silicon layer, a 1 µm thick oxide, and a 535 µm thick bulk silicon layer in FIG. 10. FIG. 11 shows a thin metal layer deposited to act as bottom electrode and patterned using photolithography. In the next step, the piezoelectric material is deposited, in this case the material is an Aluminium Nitride (AlN) layer which is deposited by sputtering and then the layer is patterned, as shown in FIG. 12. One alternative method of processing AlN layer is to deposit a bottom metal layer and AlN layer in a single sputtering chamber without breaking vacuum. In that case, the patterning of layers is performed in the reverse order, e.g. AlN layer is etched first followed by an etching of the metal. The materials can be patterned using wet or dry etch techniques. In the next step, illustrated in FIG. 13, a top metal layer is deposited and patterned, which acts as the top electrode. This can follow by deposition and pattern of the passivation layer such as silicon dioxide (not illustrated in figures) that may act as a barrier layer for liquid accessing the electrodes. Other layers, for instance to compensate the material stresses, can also be deposited but are not shown here. In the following step, as shown in FIG. 14, the device silicon is etched down to the oxide layer using different methods that can, for example, be a wet etching anisotropic or isotropic (e.g. KOH Potassium hydroxide), dry etching (e.g. DRIE—Deep Reactive Ion Etching) or combination of both or other techniques. The density, dimensions and shape (cross section) of the apertures or holes in the device silicon can be modified during processing according to the required droplets size and flow rate for a given application. For instance, the size of the aperture/hole (i.e. diameter of the exit hole) is one of the major factors defining the size of generated droplets to be dispensed. If the target droplet diameter to be produced is 3 um then the size of the exit aperture or hole must be close to 3 um. This will ensure that the majority of all droplets generated by the vibrating mesh are around 3 um in diameter. Similarly, if another application requires aerosol with average droplets of 20 um then the mesh should be fabricated with holes that have 20 um wide exit aperture/hole. Similarly the flow rate of the device can be optimized by changing the holes density and location over the device area. In the final step, as shown in FIG. 15, etching of the bulk silicon is performed using wet or dry etching techniques that is followed by the removal of the oxide layer.

It will be appreciated that the process described above demonstrates the fabrication of a single device but 10's to 100's of devices can be fabricated per single wafer (depending on the wafer size that for instance can be 300 mm in the diameter) as a typical diameter of a single device is approximately 5 mm. The entire wafer can then be diced using a mechanical saw or other dicing method allowing for an individual devices to be released. Note that the sequence of fabrication steps can be different to that described above and used interchangeably. For instance, the process can start with etching of the bulk silicon first so the entire metal/AlN/metal stack is deposited on the bottom surface of the device silicon. Also, the aperture/holes etching could be performed either from the top surface of the device silicon (as described in the example above) or from the bottom surface of the device silicon.

FIG. 16 illustrates at least one sensor/circuit configured to operate in conjunction with the monolithic integrated mesh device. The fabrication steps described in FIGS. 10 to 15 can be a post-CMOS, which means that before the device fabrication starts CMOS circuitry 80 and/or sensors 81 are fabricated within the substrate 76, for instance in bulk silicon and/or device silicon. Because all materials such as titanium, aluminium nitride, aluminium are CMOS compatible the entire fabrication process can be performed in CMOS/MEMS fabrication facility allowing for integration of advanced circuitry in highly controlled process environment. The circuitry 80 and sensors 81 can be used for device actuation and performance monitoring. For example at least one strain sensor can be integrated with the monolithic integrated mesh device.

Advantages of the monolithic approach according to the invention versus prior-art include lower cost fabrication with better tolerance and process uniformity, better reliability as there is no need for assembling of different discreet components as in prior art. Furthermore, with the monolithic approach, the mesh devices can be fabricated in existing CMOS and MEMS fabrication facilities in high volume allowing for integration with IC electronics and sensors. The following table sets out the advantages of using silicon to make the vibrating mesh of the present invention:

| Standard metal-based process | New class silicon-based process |
|---|---|
| Processing | |
| current metal-based process cannot provide sufficient process uniformity when producing small holes (<5 um) in mesh device, which results in non-uniform distribution of droplets; out of all produced meshes only some devices pass the test on droplets size and only these are selected as a valid devices; this result in reduced production yield and higher overall technology cost | silicon processing techniques have better process tolerance thus tighter hole distribution can be achieved which results in more uniform droplets/aerosol, higher fabrication yield and lower fabrication cost |
| Electronics integration | |
| current metal-based process doesn't support integration of electronic components with the mesh such as resistors, capacitors, or transistors while such integration would allow adding more functionalities to the devices | Silicon is a new class of material to be used for liquid atomization, silicon is a semiconductor material and silicon-based process allows integration of electronic components with vibrating mesh, for example, implanting resistors into the silicon mesh in high strain regions (creation of a strain gauge) would allow for monitoring the device strain and displacement level and this information can be used to improve atomization performance, reliability or creation of breath actuated nebulizer technology for more efficient treatment |
| Piezoelectric material integration (and other materials) | |
| current metal-based process doesn't support integration of piezoelectric actuator when producing mesh which results in post-process assembly of mesh and actuator; the external actuator needs to provide significant force to actuate the mesh and therefore large voltages must be used to generate sufficient displacements; this contributes to higher power consumption; also the assembly process may decrease overall reliability of the nebulizer, also the reliability of the actuator itself may be the limiting factor<br>good transfer of mechanical energy from actuator to mesh requires strong bonds | In silicon-based process the integration of mesh with piezo-actuator can be realized in a monolithic fashion (in a single fabrication process), the reliability of such monolithically integrated mesh can be better than reliability of metal mesh that is actuated with the external piezo-actuator assembled in a separate process<br>The root cause of fracture in silicon plates is different to that in metals, and is further mitigated by means of integration of piezo-material.<br>Integrated mesh has lower power required to actuate the mesh, better controllability of mesh displacement, lower fabrication cost because assembly is not required, and better reliability<br>Integrated mesh with piezo-actuator would have lower energy loss to the device housing and better energy transfer from the actuator to mesh<br>Silicon processes allows for relatively simple integration of other materials that can be used to passivated/coat the mesh to improve its properties (modify surface tension or hydrophobicity) |

It will be appreciated that a breath sensor can be integrated with silicon-based mesh, so the device only operates during predefined portions of the breath, allowing control of aerosol delivery to the lung.

The invention also covers the capability of creating a new assembly using thin film piezoelectric materials which can be deposited directly onto the MEMS aperture using standard CMOS compatible deposition techniques. Various piezoelectric materials could be used including AlN, ZnO, PZT, and PVDF. The idea is that the piezoelectric material can be deposited and patterned on the surface of the aperture substrate using microfabrication methods. The piezoelectric material can be uniquely patterned to control the mode of operation. Then using standard patterning the holes can be patterned in the piezoelectric layer and through the aperture structure, this technique can reduce power as it requires less voltage to create the same amount of displacement as the bulk ring piezoelectric, and the etch process is highly repeatable.

Applications of this type of device are many. Aperture plates for atomisation or filtration can be configured to be included in systems such as;

a) Nebulisers—wherein the aperture plate is either active or static and facilitates the atomisation of liquid fed to the aperture plate, regardless of feed rate. Nebulising systems including this technology could be used for a variety of targeting applications, including, but not limited to nasal, pulmonary, ophthalmic and laparoscopic drug delivery.

b) Such systems could include handheld configurations, for use in combination with facemask, mouthpiece or nasal cannula, or systems designed for inclusion in circuits providing ventilatory support, for example ventilator circuits, circuits making use of a supplementary gas flow and interfacing with the patient by means of endotracheal tube, face mask laryngeal mask, mouthpiece, tracheostomy, nasal mask nasal cannula et cetera. Humidification systems—wherein the aperture plate is either active or static and facilitates the atomisation of liquid fed to the aperture plate, for the purposes of increasing the level of humidification in a system. Such systems may include, but are not limited to, rooms, ventilator circuits as described above, human airways, transport vehicles, storage units et cetera.

c) Calibration equipment—wherein the aperture plate is either active or static and facilitates the atomisation of liquid fed to the aperture plate, for the purposes of generating droplets of a known size for use in the calibration of associated equipment. Such systems may include, but are not limited to, biohazard detection, smoke/particle detectors et cetera.

d) Liquid feed systems—wherein the aperture plate is either active or static and facilitates the atomisation or transport of liquids fed to the aperture plate, for the purposes of transporting a liquid bulk in a timed and controlled fashion. Such systems may include, but are not limited to, mass spectrometry system, liquid pumps, or other systems requiring an increase in the surface area of a liquid formulation for the purposes of reactions.

e) Filtration systems—wherein the aperture plate is either active or static and facilitates the filtration of fluids and separation of components from said fluid. Such systems may include, but are not limited to, food manufacturing (e.g. sugar cane filtration), systems designed to separate particles of varying sizes.

f) Printing systems—wherein the aperture plate is either active or static and facilitates the atomisation of liquid fed to the aperture plate, for the purposes of generating droplets of a known size for use in the printing process. Such systems may include, but are not limited to, ink jet printing and the application of conductive inks.

g) Spray systems—wherein the aperture plate is either active or static and facilitates the atomisation of liquid fed to the aperture plate, for the purposes of generating droplets of a known size for use in applying liquid formulations to the surfaces of target areas. Such systems may include, but are not limited to, systems spraying formulations for; the surface treatment of clothing, surface treatment of solid surfaces, surface application of liquids to medical devices, mixing of liquids, cosmetic sprays, e.g tanning products.

h) Vaporising systems—wherein the aperture plate is either active or static and facilitates the atomisation of and vaporisation of liquid fed to the aperture plate combined with a heated piezoelectric element. Such systems may include, but are not limited to, electronic cigarettes and the like.

It will be appreciated the invention provides:

reduced fabrication cost smaller apertures (limited by etch choice and material thickness)

the opportunity to manipulate aperture density, location, shape and size can be easily modified with microfabrication processes used for MEMS and CMOS, such as wet and dry etching techniques tighter fabrication tolerance, better repeatability, higher fabrication yield assembly between actuator-holder-mesh is not required—lower cost of the entire system better reliability because actuator monolithically integrated with mesh better energy transfer as there is no need for holder silicon gives possibility for integration of electronic components such as resistors and transistors that may be used as control electronics and/or sensors process flexibility in terms of using different materials and processing steps, for instance to passivated the device or coat to modify surface tension properties or hydrophobicity silicon only device can directly replace current metal-based device and use current assembly process.

In the specification the terms "comprise, comprises, comprised and comprising" or any variation thereof and the terms include, includes, included and including" or any variation thereof are considered to be totally interchangeable and they should all be afforded the widest possible interpretation and vice versa.

The invention is not limited to the embodiments hereinbefore described but may be varied in both construction and detail.

The invention claimed is:

1. An aerosol-generating device comprising:
a mesh, said mesh being a single mesh membrane comprising a plurality of apertures and
a piezoelectric material monolithically integrated with the mesh;
wherein the piezoelectric material is a CMOS compatible piezoelectric material and
wherein the piezoelectric material induces displacement of the mesh and controls a vibration frequency the mesh for atomization of a liquid to generate an aerosol.

2. The device as claimed in claim 1, wherein the mesh comprises silicon.

3. The device as claimed in claim 1, wherein the piezoelectric material comprises a thin film deposited on the mesh, wherein the piezoelectric material is bonded to the mesh at an atomic scale.

4. The device as claimed in claim 1, wherein the device is configured as a pump for pumping the liquid.

5. The device as claimed in claim 1, wherein the mesh operates in a vibrating mode.

6. The device as claimed in claim 1, wherein a size of the apertures is selected to control a droplet size of the atomized liquid.

7. The device as claimed in claim 1, wherein a location and a shape of the apertures are selected to control an aerosol of the atomized liquid.

8. The device as claimed in claim 1, wherein at least one surface of at least one aperture of the plurality of apertures is treated to alter at least one hydrophobic property of the at least one aperture of the plurality of apertures.

9. The device as claimed in claim 1, wherein the piezoelectric material covers at least a part of the mesh.

10. The device as claimed in claim 1, wherein the piezoelectric material is used to control a plurality of different resonant modes of the device.

11. The device as claimed in claim 1, wherein the piezoelectric material is adapted to be selectively patterned on the mesh to control a mode of operation of the aerosol-generating device.

12. A device as claimed in claim 1, wherein the device is configured for atomization of the liquid, wherein the plurality of apertures is made using a microfabrication process, and wherein the mesh comprises at least one of: silicon, glass, metal, ceramic, and a polymer.

13. The device as claimed in claim 1, wherein the mesh comprises a silicon mesh for atomization of the liquid through the plurality of apertures.

* * * * *